United States Patent
Mohapatra et al.

(10) Patent No.: US 10,633,360 B2
(45) Date of Patent: Apr. 28, 2020

(54) EFFICIENT PROCESS FOR THE SYNTHESIS OF ALKOXY SUBSTITUTED BENZALDEHYDES

(71) Applicant: ANTHEA AROMATICS PRIVATE LIMITED, Navi Mumbai (IN)

(72) Inventors: Manoj Kumar Mohapatra, Navi Mumbai (IN); Ramamohanrao Bendapudi, Navi Mumbai (IN); Paul Vincent Menacherry, Mumbai (IN); Vincent Paul, Mumbai (MH)

(73) Assignee: ANTHEA AROMATICS PRIVATE LIMITED, Navi Mumbai (IN)

( * ) Notice: Subject to any disclaimer, the term of this patent is extended or adjusted under 35 U.S.C. 154(b) by 89 days.

(21) Appl. No.: 15/538,012

(22) PCT Filed: Apr. 29, 2015

(86) PCT No.: PCT/IB2015/053112
§ 371 (c)(1),
(2) Date: Jun. 20, 2017

(87) PCT Pub. No.: WO2016/103058
PCT Pub. Date: Jun. 30, 2016

(65) Prior Publication Data
US 2017/0349566 A1 Dec. 7, 2017

(30) Foreign Application Priority Data
Dec. 23, 2014 (IN) .......................... 4124/MUM/2014

(51) Int. Cl.
*C07D 317/68* (2006.01)
*C07D 317/54* (2006.01)
*C07C 45/56* (2006.01)

(52) U.S. Cl.
CPC .......... *C07D 317/54* (2013.01); *C07C 45/565* (2013.01); *C07D 317/68* (2013.01)

(58) Field of Classification Search
CPC .................................................. C07D 317/68
See application file for complete search history.

(56) References Cited

U.S. PATENT DOCUMENTS 2,916,499 A 12/1959 Blair
4,335,263 A 6/1982 Minai
4,605,749 A 8/1986 Buchman et al.
4,942,240 A 7/1990 Bluthe et al.
8,618,335 B2 12/2013 Doi

FOREIGN PATENT DOCUMENTS

| BE | 877911 | 11/1979 | |
|---|---|---|---|
| CN | 101899033 | 12/2010 | |
| EP | 000537 | 7/1978 | |
| EP | 0031253 | 7/1981 | |
| GB | 1538214 | 1/1979 | |
| JP | 3282338 | 3/2002 | |
| WO | WO-2008023836 A1 * | 2/2008 | ............ C07C 45/00 |

OTHER PUBLICATIONS

International Preliminary Report on Patentability. PCT/IB2015/053112. (Year: 2016).*
International Search Report on Patentability dated Feb. 24, 2016 for PCT/IB2015/053112.
International Search Report and Written Opinion dated Aug. 31, 2015 for PCT/IB2015/053112.
Examination Report dated Mar. 7, 2018 for Indian Priority application No. 4124/MUM/2014.
E:Profft et al.:"Uber die Chlormethylierung von Aloxybenzolen und die Gewinnung der entsprechenden Benzaldehyde", Journal fur Parktische Chemie, vol. 3, Nov. 2004.
Angyal S J: "The Sommelet Reaction", Organic Reaction, XX, XX vol. 8. Jan. 1, 1954.

* cited by examiner

*Primary Examiner* — Noble E Jarrell
*Assistant Examiner* — John S Kenyon
(74) *Attorney, Agent, or Firm* — Silvia Salvadori

(57) ABSTRACT

The present invention relates to the synthesis of alkoxy substituted benzaldehydes obtained from the corresponding alkoxy substituted benzenes. Alkoxy substituted benzaldehydes are products of broad commercial interest and are used as end products and intermediates in flavor and fragrance applications and pharmaceutical ingredients. For example, 3,4-methylendioxy-benzaldehyde (also known as heliotropin or piperonal) is used widely both as a end product and intermediate for the above mentioned applications. Other examples include 3,4-dimethoxybenzaldehyde, 3,4,5-trimethoxybenzaldehyde and 3,4-ethylenedioxybenzene which are intermediates in the synthesis of active pharmaceutical intermediates.

11 Claims, No Drawings

EFFICIENT PROCESS FOR THE SYNTHESIS OF ALKOXY SUBSTITUTED BENZALDEHYDES

RELATED APPLICATIONS

This application is the US national phase application of international application number PCT/IB2015/053112, filed 29 Apr. 2015, which designates the US and claims priority to Indian application 4124/MUM/2014 filed 23 Dec. 2014, the contents of each of which are hereby incorporated by reference as if set forth in their entireties.

FIELD OF TECHNOLOGY

Disclosed herein is an efficient, economical, industrially advantageous, straight-through process for the synthesis of alkoxy substituted benzaldehydes of Formula I in substantially pure form and high yield, from the corresponding alkoxy substituted benzenes of Formula II.

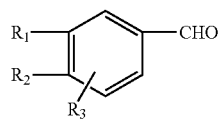

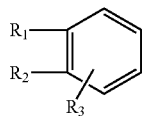

Wherein $R_1$, $R_2$ and $R_3$ are independent of each other, $R_2$ represents alkoxy group —OR, wherein R is a substituted or unsubstituted $C_1$-$C_4$ alkyl group, substituted or unsubstituted $C_3$-$C_6$ cycloalkyl group, or $R_1$ and $R_2$ together jointly form an alkylenedioxy group represented by —O—($CH_2$)n-O— wherein n is 1, 2, 3 or 4, $R_1$ represents H, R or —OR, wherein R is a substituted or unsubstituted $C_1$-$C_4$ alkyl group, substituted or unsubstituted $C_3$-$C_6$ cycloalkyl group, or $R_1$ and $R_2$ together jointly form an alkylenedioxy group represented by —O—($CH_2$)n-O— wherein n is 1, 2, 3 or 4, and $R_3$ is a substituent at any position of aromatic ring other than position 1,3 and 4 and represents H, R, —OR, wherein R is a substituted or unsubstituted $C_1$-$C_4$ alkyl group or substituted or unsubstituted $C_3$-$C_6$ cycloalkyl group, or R3 represents halogen selected from Cl, Br, I, or nitrogen containing group selected from CN, $NO_2$, $NH_2$, —$CONH_2$.

Herein straight-through chemical process is defined as a sequence of reactions which are carried out in-situ, preferably in a single solvent medium, and which does not require solvent recovery and/or isolation/purification at intermediate stages to give the desired product in substantially pure form and high yield.

When $R_1$ and $R_2$ together form a methylenedioxy group and $R_3$ is H then the compound of Formula I represents heliotropin, also referred as piperonal or 3,4-methylenedioxybenzaldehyde which is represented by a compound of Formula IV. The said compound of Formula IV is prepared by using methylenedioxybenzene of Formula III as a starting material.

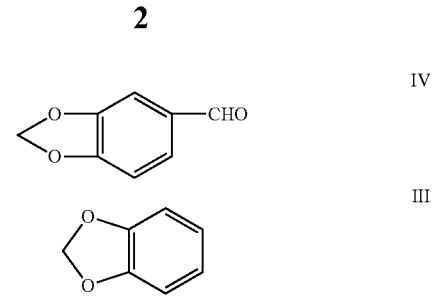

The process disclosed herein allows the use of a single organic solvent as reaction medium, and does not require removal of solvent and/or isolation/purification at any intermediate stage, thereby minimizing unit operations and handling losses during plant-scale operations. As a result, under these simplified process conditions, the alkoxy substituted benzaldehydes of Formula I can be obtained in substantially pure form and high yield starting from the corresponding alkoxy substituted benzenes of Formula II. For example when aromatic hydrocarbon such as toluene is selected as a solvent then methylenedioxybenzene of Formula III is converted in a straight-through chemical process into substantially pure (greater than 95%) heliotropin of Formula IV in about 80% yield without solvent recovery, and/or isolation/purification at intermediate stages.

BACKGROUND

Alkoxy substituted benzaldehydes of Formula I are an important class of compounds which find varied use in the chemical, agrochemicals, pharmaceutical and cosmetic industries, and these are also used as intermediates in the preparation of other known compounds. For example, 3,4-methylenedioxy benzaldehyde, also referred as heliotropin or piperonal, of Formula IV is used in fragrance and flavor applications, and also as an intermediate for the preparation of drug molecules such as Tadalafil™, as well as agrochemicals. Other examples include 3,4-dimethoxybenzaldehyde, 3,4,5-trimethoxybenzaldehyde and 3,4-ethylenedioxybenzene which are intermediates in the synthesis of active pharmaceutical intermediates. The required purity of the product depends upon the specific application; however it is preferable to have the material in substantially pure form (greater than 95%).

The conventional process for preparing heliotropin (piperonal), disclosed in the prior art comprises isomerizing and oxidizing safrole contained in the essential oil of Octoea Cym barum (disclosed in U.S. Pat. No. 2,916,499). However, this process has the drawback that the supply and the price of the raw material are unsteady due to its dependence upon the natural resources. Hence processes based on synthetic raw materials are preferable.

There are various chemical methods disclosed in the prior art for the synthesis of alkoxy substituted benzaldehydes.

Japanese patent application 156867/77 discloses a process for the preparation of heliotropin, comprising formylation of methylenedioxybenzene using N-methyl formanilide. However, 50 to 60% of 1,2-methylenedioxybenzene is recovered, and the energy consumption is very high, and therefore this is not advantageous as an industrial process.

J. Gen. Chem 8, 975 (1938) and British Pat. 1538214 disclose chloromethylation process for the preparation of heliotropin comprising chloromethylation of methylenedioxybenzene to obtain 3,4-methylenedioxybenzyl chloride which in turn is reacted with alkali metal salt of 2-nitropropane to obtain heliotropin. The yield of end product is 55-60% based on methylenedioxybenzene and also a large amount of tar like material is formed as a byproduct.

BE877911A1 discloses a process for converting methylenedioxybenzene into mandelic acid which in turn is converted into the corresponding benzaldehyde. The yield obtained is very low.

U.S. Pat. No. 4,942,240A discloses a process for the preparation of benzaldehyde and analogues thereof comprising reacting aromatic halide with a mixture of hydrogen and carbon monoxide in the presence of a noble metal based catalyst.

U.S. Pat. No. 4,605,749A discloses a process for the preparation of aromatic aldehydes wherein corresponding aryl halide is used as a starting material. Process disclosed therein comprises reacting aryl halide with carbon monoxide at super atmospheric pressure in the presence of a hydrogen donor, base and a catalyst.

U.S. Pat. No. 4,335,263A discloses a process for the preparation of aromatic aldehydes wherein a substituted benzyl halide obtained as an intermediate is converted into corresponding benzaldehyde by oxidizing the said benzyl halide. The process disclosed therein comprises of multiple steps for the preparation of methylenedioxybenzyl halide and the end product obtained is in 55.8% yield based on w/w in respect of methylenedioxybenzyl bromide. There is no mention of purity and yield of heliotropin.

JP3282338B2 discloses a process for the preparation of heliotropin wherein methylenedioxybenzyl chloride is oxidized with a hypohalogenous acid in the presence of a phase transfer catalyst in a two-phase system of an organic solvent and water.

JP62005977A also discloses the process for the preparation of heliotropin by electrolyzing methylenedioxybenzyl chloride by using an electrolyte like sodium hydroxide.

U.S. Pat. No. 8,618,335 discloses a process for preparing an aromatic aldehyde compound by reacting the corresponding aromatic methyl alcohol with peroxide in the presence of metal compound of tungsten or molybdenum, and either a quarternary ammonium salt or organic phosphonium salt.

JP54135770 discloses a process for the preparation of heliotropin comprising reacting methylenedioxybenzene with formaldehyde and HCl to obtain methylenedioxybenzyl chloride which is isolated and reacted with hexamethylenetetramine using chloroform as a solvent to obtain a salt also referred as complex. The said salt is isolated by filtration process and after dissolving in acetic acid is reacted with ammonia to obtain heliotropin. There is no mention of purity of the product obtained there from. The process disclosed in said patent comprises multiple operations such as solvent recovery and isolation/purification of intermediates, after each reaction step and also requires the use of more than one solvent, and requires the use of industrially unsafe chloroform as a reaction medium. There is no mention of the purity of the final isolated product.

WO2008023836 discloses a process for the preparation of heliotropin comprising reacting methylenedioxybenzene with formaldehyde and aqueous HCl in toluene to obtain piperonyl chloride in 85% yield based on internal online GC standard without mention of yield of isolated material. The solvent is distilled off and the said piperonyl chloride is reacted in a second reaction medium of acetic acid with hexamethylenetetramine in molar ratio of 0.25 moles to 1.0 mole per mole of piperonyl chloride to obtain the complex of Formula A which is subsequently decomposed to obtain piperonal. The piperonal obtained is isolated by extraction with ethyl acetate. The process disclosed therein involves the use of multiple solvents, as well as isolation/purification at intermediate stages. Moreover, the purity of the final product obtained is not mentioned.

All the processes disclosed in the prior art and described hereinabove require multiple unit operations such as solvent recovery and/or isolation/purification of intermediates, or are otherwise unsuitable for large-scale industrial production. This necessitates the development of an improved process for the preparation of alkoxy substituted benzaldehydes which minimizes the number of unit operations, provides better yield and higher purity of product and minimizes the solvent usage in comparison with the processes disclosed therein in the prior art, and which is suitable for industrial scale preparation of alkoxy substituted benzaldehydes.

The object of the present invention is to provide a solution to the technical problems associated with the prior art. Keeping the said object in view, the present invention provides an industrially viable and economical process thereby eliminating the above-mentioned shortcomings associated with the processes disclosed in the prior art for the preparation of alkoxy substituted benzaldehydes of Formula I.

OBJECT AND SUMMARY OF THE INVENTION

The inventors of the present invention disclose herein an efficient and selective process for the preparation of alkoxy substituted benzaldehydes in substantially pure form and high yield, from the corresponding alkoxy substituted benzene compounds of Formula II, comprising the use of a single solvent in a straight-through process and without solvent recovery, isolation and/or purification at any intermediate stage.

The first aspect of the present invention is to provide an improved straight-through process for the preparation of alkoxy substituted benzaldehydes of Formula I starting from the corresponding alkoxy substituted benzenes of Formula II, wherein substituents $R_1$, $R_2$ and $R_3$ are same as stated hereinabove, in substantially pure form and in high yield.

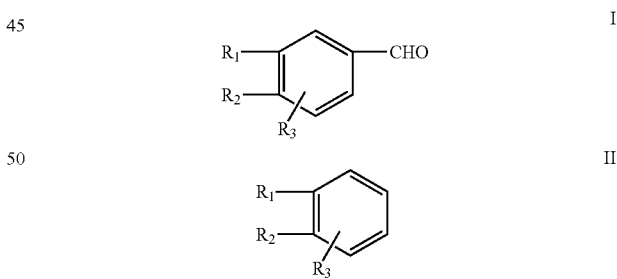

The second aspect of the present invention is the use of a single solvent in a straight-through process, and eliminating the need for solvent recovery during intermediate stages, thereby reducing the number of unit operations on plant scale, minimizing handling losses and increasing efficiency.

The third aspect of the present invention is that it does not require the isolation and/or purification at any intermediate stage thereby reducing the unit operations, minimizing handling losses and increasing efficiency.

The fourth aspect of the present invention is to provide an improved, economical and industrially viable straight-through chemical process for the preparation of heliotropin of Formula IV in of more than about 95% purity in about 80% yield.

The fifth aspect of the present invention is to provide an improved, economical and industrially viable straight-through chemical process for the preparation of heliotropin of Formula IV of more than about 95% purity in about 80% yield starting from methylenedioxybenzene of Formula III, comprising use of a single solvent for all the reaction steps, and eliminating the need for isolation and/or purification at any intermediate stage.

The sixth aspect of the present invention is to provide an improved, economical and industrially viable straight-through chemical process for the preparation of 3,4-dimethoxybenzaldehyde (also referred as veratraldehyde) of Formula V, comprising using a single solvent for all the reaction steps and eliminating the need for isolation and/or purification at any intermediate stage to obtain substantially pure final product in good yield.

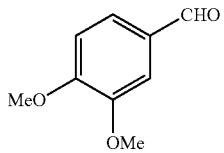

[V]

The seventh aspect of the present invention is to provide an improved, economical and industrially viable straight-through chemical process for the preparation of 3,4,5-trimethoxybenzaldehyde of Formula VI, comprising using a single solvent for all the reaction steps, and eliminating the need for isolation and/or purification at any intermediate stage to obtain substantially pure final product in good yield.

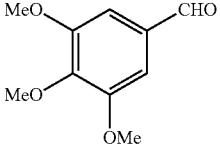

[VI]

Advantages Over the Prior Art

The process disclosed herein has the following distinct advantages over the prior art:
1. An economical and industrially viable straight-through chemical process for the preparation of alkoxy substituted benzaldehydes of Formula I in substantially pure form and high yield, from the corresponding alkoxy substituted benzenes of Formula II without isolation of the corresponding benzyl halide of Formula VII and the complex of Formula VIII formed by reacting the said benzyl halide with hexamethylenetetramine.

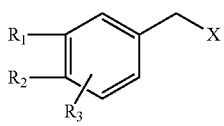

VII

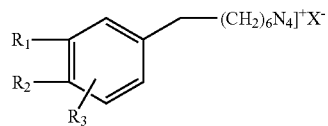

VIII $R_1$, $R_2$ and $R_3$ are same as in compound of formula I stated hereinabove and X is selected from the halo group Cl, Br or I.
2. The use of a single solvent throughout the process, which need not be removed during the entire process till the isolation of desired final product.
3. The elimination of unit operations such as solvent recovery, isolation and purification at intermediate stages, thereby making the process more economical, operational friendly on industrial scale and the product obtained is in good yield and in substantially pure form.
4. Preparation of heliotropin of pharmaceutical and perfumery grade quality having more than 95% purity in more than 80% yield using methylenedioxybenzene as a starting material.

SUMMARY OF THE INVENTION

Disclosed herein is an efficient, economical, industrially advantageous straight-through process for the synthesis of alkoxy substituted benzaldehydes of Formula I in substantially pure form and high yield, starting from the corresponding compound of Formula II.

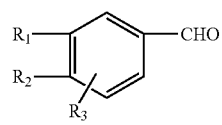

I

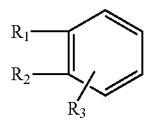

II

Wherein $R_1$ and $R_2$ and $R_3$ are same as disclosed hereinabove.

When $R_1$ and $R_2$ together form a methylenedioxy group and $R_3$ is H, then the compound of Formula I represent heliotropin also referred as piperonal or 3,4-methylenedioxybenzaldehyde, and is represented by a compound of Formula IV. The said compound of Formula IV is prepared by using methylenedioxybenzene of Formula III as a starting material.

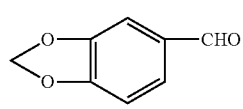

IV

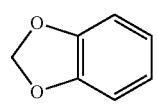

III

The process disclosed herein may be carried out in a single solvent, and does not require removal of solvent and/or isolation/purification at any intermediate stage, which minimizes the unit operations at plant scale and reduces handling loss, thereby resulting in high yield of substantially pure alkoxy substituted benzaldehydes of Formula I.

By suitable selection of solvent, the compound of Formula II is converted into corresponding alkoxy substituted benzaldehyde of substantial purity in high yield.

For example when organic solvent, preferably aromatic hydrocarbon solvent such as toluene is selected as a solvent then methylenedioxybenzene of Formula III is converted in a straight-through chemical process to give heliotropin of Formula IV in substantially pure form (greater than 95% purity) and in high yield (about 80%). Herein straight-through chemical process is defined as a sequence of reactions which are carried out in-situ, preferably in a single solvent medium, and which does not require solvent recovery and/or isolation/purification at intermediate stages, to give the desired product in substantially pure form and high yield.

DETAILED DESCRIPTION

Unless otherwise specified all parts and percentages set forth herein are weight percentages. Unless otherwise stated as used herein the term "a" or "an" include one or more components also referred as reactants or materials or solvent. The present invention may comprise, consist of, or consist essentially of the reaction or processing steps set forth herein, unless otherwise stated.

Reference will now be made in detail to the preferred embodiments of the invention. This invention may, however, be embodied in many different forms and should not be construed as limited to the embodiments set forth herein. In addition, and as well be appreciated by one skilled in the art, the invention may be embodied as a method, system or process.

It is also to be understood that the technology disclosed herein is for the purpose of describing particular embodiments only, and is not intended to be limiting.

The term about means±10%.

The term substantially pure means purity greater than 95%.

The present invention relates to an industrially acceptable improved process for the preparation of alkoxy substituted aldehydes of Formula I. The present invention not only reduces process steps and minimizes unit operation but also minimizes yield loss by avoiding isolation and/or purification of intermediates to manufacture alkoxy substituted aldehydes of Formula I in substantially pure form and in high yield.

In one embodiment disclosed herein is a straight-through chemical process for the preparation of alkoxy substituted benzaldehydes of Formula I, wherein $R_1$, $R_2$ and $R_3$ are same as described hereinbefore;

and comprising:

contacting starting material compound of Formula II with formaldehyde and an acid HX (wherein X is Cl, Br or I) in an organic solvent to obtain the compound of Formula VII;

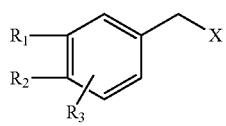

VII

The said process for the preparation of compound of Formula VII is referred as halomethylation;

the reaction mass obtained hereinabove containing compound of Formula VII as such without isolation and/or purification, is contacted with hexamethylenetetramine at about 50° C. to about 100° C. preferably at about 80° C. to obtain a complex of Formula IX;

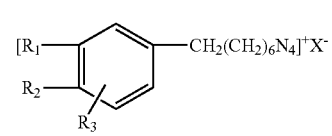

IX to the reaction mass without isolating complex of Formula IX obtained hereinabove is added an acid or base or salt selected from the group comprising aqueous acetic acid, or a mixture of aqueous acetic acid and mineral acids selected from the group comprising phosphoric acid, sulfuric acid, hydrochloric acid, nitric acid or mixtures thereof, or a mixture of organic acids selected from the group comprising acetic acid and chloroacetic acid and the likes, or a mixture of aqueous acetic acid and alkali metal salts selected from the group comprising sodium acetate or sodium phosphates and the likes or mixture thereof, or some combination of the above wherein the initial acid concentration is in the range of about 20% to about 70%, to obtain a biphasic reaction mass;

the said biphasic reaction mass obtained hereinabove is maintained in the acidic range of pH of about 2 to about 6 during reaction, and the said biphasic reaction mass is digested comprising heating at about 50° C. to about 110° C., preferably at about 80° C. to about 90° C. for about 5 to about 15 hours preferably about 8 hours, so as to decompose the compound of Formula IX to produce the corresponding alkoxy substituted benzaldehyde of Formula I;

following which the organic solvent phase containing the alkoxy substituted benzaldehyde of Formula I is separated from the aqueous Phase by decantation. If required the aqueous phase can be further extracted with the same organic solvent. The organic solvent extracts are combined and solvent is separated and the product is purified to the required purity by standard purification process preferably in a distillation column.

Herein the process for converting the complex of Formula IX into the corresponding alkoxy substituted benzaldehyde of Formula I is referred as decomposition of the said complex of Formula IX.

The reaction steps described in an embodiment for the straight-through process for the preparation of compound of Formula I are performed in an organic solvent. There is no particular restriction on the nature of the organic solvent to be employed, provided that it has no adverse effect on the reaction or on the reagents involved. Examples of suitable solvents include aromatic hydrocarbons selected from the group comprising benzene, toluene, xylene, and mixtures thereof.

The acid represented by formula HX used herein for the preparation of compound of Formula VII is selected from HCl, HBr and HI.

Herein contacting means reacting, adding, refluxing, mixing, stirring and the like.

In another embodiment herein is disclosed an in-situ process for the preparation of heliotropin of Formula IV comprising:

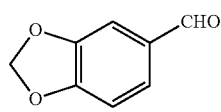

[IV]

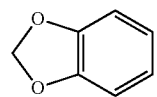

[III]

halomethylation of starting material comprising contacting said starting material compound of Formula III with formaldehyde and an acid HX (wherein X is Cl, Br or I) in an organic solvent to obtain the compound of Formula X;

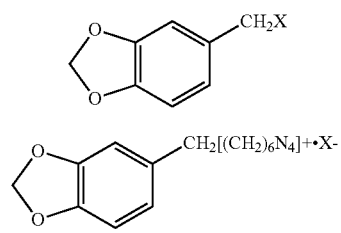

[X]

[XI]

the reaction mass obtained hereinabove containing compound of Formula X is, without isolating compound of Formula X, contacted with hexamethylenetetramine at about 50° C. to about 100° C. preferably at about 80-90° C. and more preferably at about 80° C. to obtain a complex of Formula XI;

to the reaction mass obtained hereinabove, without isolating the complex of Formula XI, is added an acid or base or salt selected from the group comprising aqueous acetic acid, or a mixture of aqueous acetic acid and mineral acids selected from the group comprising phosphoric acid, sulfuric acid, hydrochloric acid, nitric acid or mixtures thereof, or a mixture of organic acids selected from the group comprising acetic acid and chloroacetic acid and the likes, or a mixture of aqueous acetic acid and alkali metal salts selected from the group comprising sodium acetate or sodium phosphates and the likes or mixture thereof, or some combination of the above wherein the initial acid concentration is in the range of about 20% to about 70%, to obtain a biphasic reaction mass;

the said biphasic reaction mass obtained hereinabove is maintained in the acidic range of pH of about 2 to about 6, during reaction, and the said biphasic reaction mass in-situ is digested comprising heating at about 50° C. to about 100° C., preferably at about 80° C. for about 5 to about 15 hours preferably about 8 hours, so as to decompose the compound of Formula XI to produce the corresponding substantially pure alkoxy substituted benzaldehyde of Formula IV of more than 95% purity in about 80% yield.

Herein the process for converting the complex of Formula XI into the aromatic benzaldehyde of Formula IV also referred as heliotropin, 3,4-methylenedioxy benzaldehyde or piperonal is referred as decomposition of the said complex of Formula XI.

The reaction steps described in an embodiment for the in-situ process for the preparation of compound of Formula IV are performed in an organic solvent. There is no particular restriction on the nature of the organic solvent to be employed, provided that it has no adverse effect on the reaction or on the reagents involved. Examples of suitable solvents include aromatic hydrocarbons selected from the group comprising benzene, toluene, xylene, and mixtures thereof. Preferably the organic solvent used in this case is toluene.

The acid represented by formula HX used herein for the preparation of compound of formula X is selected from HCl, HBr and HI. Preferably the acid used in this case is HCl.

In still another embodiment herein is disclosed an in-situ process for the preparation of compound of Formula V comprising:

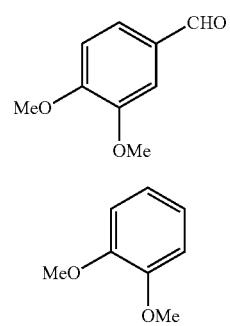

[V]

[XII]

halomethylation of starting material comprising contacting said starting material compound of XII with formaldehyde and an acid HX (wherein X is Cl, Br or I) in an organic solvent to obtain the compound of Formula XIII;

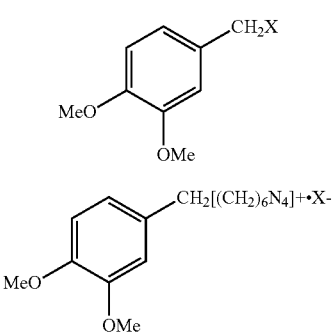

[XIII]

[XIV]

the reaction mass obtained hereinabove containing compound of formula XIII is, without isolating compound of formula XIII in-situ, contacted with hexamethylene tetramine at about 50° C. to about 100° C. preferably at about 80° C. to obtain a complex of Formula XIV;

to the reaction mass obtained hereinabove, without isolating complex of Formula XIV, is added an acid or base or salt selected from the group comprising aqueous acetic acid, or a mixture of aqueous acetic acid and mineral acids selected from the group comprising phosphoric acid, sulfuric acid, hydrochloric acid, nitric acid or mixtures thereof, or a mixture of organic acids selected from the group comprising acetic acid and chloroacetic acid and the likes, or a mixture of aqueous acetic acid and alkali metal salts selected from the group comprising sodium acetate or sodium phosphates and the likes or mixture thereof, or some combination of the above wherein the initial acid concentration is in the range of about 20% to about 70%, to obtain a biphasic reaction mass;

the said biphasic reaction mass obtained hereinabove is maintained in the acidic range of pH of about 2 to about 6 during reaction, and the said biphasic reaction mass in-situ is digested comprising heating at about 40° C. to about 100° C., preferably at about 80° C. for about 5 to about 15 hours preferably about 8 hours, so as to decompose the compound of Formula XIV to produce the corresponding alkoxy substituted benzaldehyde of Formula V. The organic solvent phase is separated and the aqueous phase is optionally extracted with the same organic solvent. The organic solvent extracts are combined and solvent is separated and the product is purified to the required purity in a distillation column.

Herein the process for converting the complex of Formula XIV into the alkoxy substituted benzaldehyde of Formula V is referred as decomposition of the said complex of Formula XIV.

The reaction steps described in an embodiment for the straight-through chemical process for the preparation of compound of Formula V are performed in an organic solvent. There is no particular restriction on the nature of the organic solvent to be employed, provided that it has no adverse effect on the reaction or on the reagents involved. Examples of suitable solvents include aromatic hydrocarbons selected from the group comprising benzene, toluene, xylene, and mixtures thereof. Preferably the organic solvent used in this case is toluene.

The acid represented by formula HX used herein for the preparation of compound of formula VIII is selected from HCl, HBr and HI. Preferably the acid used in this case is HCl.

In still another embodiment disclosed herein is a process for the preparation of compound of Formula VI comprising:

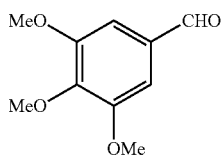
[VI]

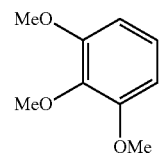
[XV]

Halomethylation of starting material comprising contacting said starting material compound of Formula XV with formaldehyde and an acid HX (wherein X is Cl, Br or I) in an organic solvent to obtain the compound of Formula XVI;

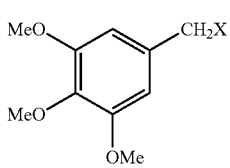
[XVI]

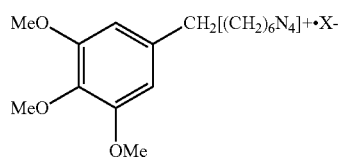
[XVII]

the reaction mass obtained hereinabove containing compound of Formula XVI is, without isolating compound of Formula XVI, contacted with hexamethylene tetramine at about 50° C. to about 100° C., preferably at about 80° C. to obtain a complex of Formula XVII;

to the reaction mass obtained hereinabove, without isolating complex of Formula XVII, is added an acid or base or salt selected from the group comprising aqueous acetic acid, or a mixture of aqueous acetic acid and mineral acids selected from the group comprising phosphoric acid, sulfuric acid, hydrochloric acid, nitric acid or mixtures thereof, or a mixture of organic acids selected from the group comprising acetic acid and chloroacetic acid and the likes, or a mixture of aqueous acetic acid and alkali metal salts selected from the group comprising sodium acetate or sodium phosphates and the likes or mixture thereof, or some combination of the above wherein the initial acid concentration is in the range of about 20% to about 70%, to obtain a biphasic reaction mass;

the said biphasic reaction mass obtained hereinabove is maintained in the acidic range of pH of about 2 to about 6 during reaction, and the said biphasic reaction mass insitu is digested comprising heating at about 40° C. to about 100° C., preferably at about 80° C. for about 5 to about 15 hours preferably about 8 hours, so as to decompose the compound of Formula XVII and produce the corresponding aromatic benzaldehyde of Formula VI. The organic solvent phase is separated and the aqueous phase is optionally extracted with the same organic solvent. The organic solvent extracts are combined and solvent is separated and the product is purified to the required purity in a distillation column.

Herein the process for converting the complex of Formula XVII into the alkoxy substituted benzaldehyde of formula VI is referred as decomposition of the said complex of Formula XVII.

The reaction steps described in an embodiment for the straight-through process for the preparation of compound of Formula VA are performed in an organic solvent. There is no particular restriction on the nature of the organic solvent to be employed, provided that it has no adverse effect on the reaction or on the reagents involved. Examples of suitable solvents include aromatic hydrocarbons selected from the group comprising benzene, toluene, xylene, and mixtures thereof. Preferably the organic solvent used in this case is toluene.

The acid represented by formula HX used herein for the preparation of compound of formula VIII is selected from HCl, HBr and HI. Preferably the acid used in this case is HCl.

The following non limiting examples are provided to illustrate further the present invention. It will be apparent to those skilled in the art many modifications, alterations, variations to the present disclosure, both to materials, method and reaction conditions, may be practiced. All such modifications, alterations and variations are intended to be within the spirit and scope of the present inventions. It

WORKING EXAMPLES

The present invention is further described according to the following working examples. The analysis was done by the gas chromatography, using a ZB-1 capillary column, 0.25 micrometer of thickness×30 m, Phenomenex (USA) make.

Example 1: Synthesis of Piperonal

Paraformaldehyde (180 g), 30% hydrochloric acid (730 g), toluene (1.0 kg) and methylenedioxybenzene (488 g) were charged into a 3 litre glass reactor. Hydrogen chloride gas was passed rapidly at about −10° C. through the reaction medium for 5 to 10 hours. The GC content of the chloromethyl derivative was ~90% at this stage. The aqueous portion was drained off and the organic portion containing MDB-Cl was digested with hexamine (560 g) at about 80° C. till the content of the chloromethyl derivative was less than 0.5% by GC analysis. 50% aqueous acetic acid (1.3 kg) was added to the resulting hexamine complex and the reaction mass was digested at about 80° C. for 6 to 8 hours. The aqueous portion was drained off. The toluene was recovered, and the crude product was distilled to separate a fraction containing unreacted methylenedioxybenzene (25 g) and piperonal of purity greater than 95% (309 g).

Example 2: Synthesis of Piperonal

Paraformaldehyde (180 g), 30% hydrochloric acid (730 g), toluene (1 kg) and methylenedioxybenzene (488 g) were charged into a 3 litre glass reactor. Hydrogen chloride gas was passed rapidly at about −10° C. through the reaction medium for 5 to 10 hours. The GC content of the chloromethyl derivative was ~90% at this stage. The aqueous portion was drained off and the organic portion containing MDB-Cl was digested with hexamine (670 g) at about 80° C. till the content of the chloromethyl derivative was less than 0.5% by GC analysis. 50% aqueous acetic acid (1.3 kg) was added to the resulting hexamine complex and the reaction mass was digested at about 80° C. for 6 to 8 hours. The aqueous portion was drained off. The solvent was recovered, and the crude product was distilled to separate a fraction containing unreacted methylenedioxybenzene (25 g) and piperonal of purity greater than 95% by GC analysis (380 g).

Example 3: Synthesis of Piperonal

Paraformaldehyde (180 g), 30% hydrochloric acid (730 g), toluene (1 kg) and methylenedioxybenzene (488 g) were charged into a 3 litre glass reactor. Hydrogen chloride gas was passed rapidly at about −10° C. through the reaction medium for 5 to 10 hours. The GC content of the chloromethyl derivative was ~90% at this stage. The aqueous portion was drained off and the organic portion containing MDB-Cl was digested with hexamine (750 g) at about 80° C. till the content of the chloromethyl derivative was less than 0.5% by GC analysis. 50% aqueous acetic acid (1.5 kg) was added to the resulting hexamine complex and digested at about 80° C. for 6 to 8 hours. The aqueous portion was drained off. The solvent was recovered, and the crude product was distilled to separate a fraction containing unreacted methylenedioxybenzene (25 g) and piperonal of purity greater than 95% by GC analysis (365 g).

Example 4: Synthesis of Piperonal

Paraformaldehyde (180 g), 30% hydrochloric acid (730 g), toluene (1 kg) and methylenedioxybenzene (488 g) were charged into a 3 litre glass reactor. Hydrogen chloride gas was passed rapidly at about −10° C. through the reaction medium for 5 to 10 hours. The GC content of the chloromethyl derivative was ~90% at this stage. The aqueous portion was drained off and the organic portion containing MDB-Cl was digested with hexamine (1.0 kg) at about 80° C. till the content of the chloromethyl derivative was less than 0.5% by GC analysis. 50% aqueous acetic acid (1.7 kg) was added to the resulting hexamine complex and the reaction mass was digested at about 80° C. for 6 to 8 hours. The aqueous portion was drained off. The solvent was recovered, and the crude product was distilled to separate a fraction containing unreacted methylenedioxybenzene (25 g) and piperonal of purity greater than 95% by GC analysis (370 g).

Example 5: Procedure for 3,4,5-Trimethoxybenzaldehyde

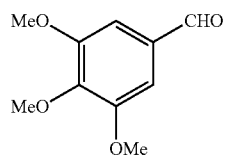

[VI]

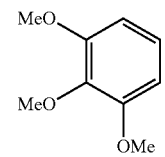

[XV]

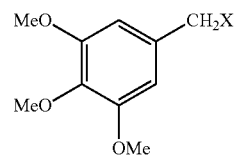

[XVI]

Paraformaldehyde (45 g), 30% hydrochloric acid (182 g) and 1,2,3-trimethoxybenzene (168 g) and toluene (1680 g) were charged into a 3 litre glass reactor. Hydrogen chloride gas was passed rapidly through the reaction medium at about 10° C. till the corresponding benzyl chloride (formula VII) was ~90% by GC analysis. The aqueous portion was drained off and the organic portion was digested with hexamine (168 g) at about 90° C. till the benzyl chloride (VII) content was less than 1.0% by GC analysis. 50% aqueous acetic acid (360 g) was added to the resulting hexamine complex and the reaction mass was digested at about 80° C. for 6 to 8 hours. The aqueous portion was drained off and the organic portion was concentrated and the crude product was distilled to obtain 3,4,5-Trimethoxybenzaldehyde of purity greater than 95% by GC analysis (130 g).

Example 6: Procedure for 3,4,-Dimethoxybenzaldehyde

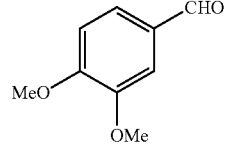 [V]

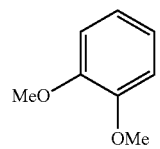 [XII]

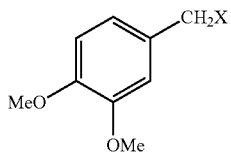 [XIII]

Paraformaldehyde (45 g), 30% hydrochloric acid (182 g), 1,2-dimethoxybenzene (138 g) and toluene (1380 g) were charged into a 3 litre glass reactor. Hydrogen chloride gas was passed rapidly through the reaction medium at about 10° C. till the corresponding benzyl chloride (formula VII) was ~90% by GC analysis. The aqueous portion was drained off and the organic portion was digested with hexamine (168 g) at about 90° C. till the benzyl chloride (VII) content was less than 1.0% by GC analysis. 50% aqueous acetic acid (360 g) was added to the resulting hexamine complex and the reaction mass was digested at about 80° C. for 6 to 8 hours. The aqueous portion was drained-off and the organic portion was concentrated and the crude product was distilled to obtain the 3,4-dimethoxybenzaldehyde of purity greater than 95% by GC analysis (110 g).

Those skilled in the art to which the present invention pertains may make modifications employing principles of the present invention resulting in other embodiments without departing from its spirit or characteristics, particularly upon considering the foregoing teachings. Accordingly, the described embodiments are to be considered in all respects only as illustrative, and not restrictive, and scope of the present invention is, therefore, is indicated by the appended claims rather than the foregoing description. Consequently while the present invention has been described with reference to particular embodiments, modification of structure, sequence, materials and the like apparent to those skilled in the art still fall within the scope of the invention as claimed by the applicant.

We claim:

1. A process for the preparation of alkoxy substituted benzaldehydes of Formula 1 from corresponding alkoxy benzenes of Formula II,

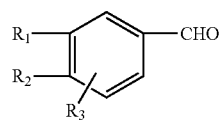 I

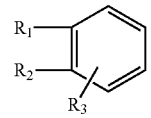 II wherein:

$R_1$, $R_2$ and $R_3$ are independent of each other, $R_2$ represents alkoxy group —OR, wherein R is a substituted or unsubstituted C1-C4 alkyl group, substituted or unsubstituted C3-C6 cycloalkyl group, or $R_1$ and $R_2$ together jointly form an alkylenedioxy group represented by —O—(CH2)n-O— wherein n is 1, 2, 3 or 4, $R_1$ represents H, R or —OR, wherein R is a substituted or unsubstituted C1-C4 alkyl group, substituted or unsubstituted C3-C6 cycloalkyl group, or $R_1$ and $R_2$ together jointly form an alkylenedioxy group represented by —O—(CH2)n-O— wherein n is 1, 2, 3 or 4, and $R_3$ is a substituent at any position of aromatic ring other than position 1,3 and 4 and represents H, R, —OR, wherein R is a substituted or unsubstituted C1-C4 alkyl group, or substituted or unsubstituted C3-C6 cycloalkyl group, or $R_3$ represents halogen selected from Cl, Br, I, or nitrogen containing group selected from CN, NO2, NH2, —CONH2, in a straight-through chemical process, said process comprising the steps of:

a) halomethylation of starting material represented by compound of Formula II in an organic solvent to obtain the compound of Formula VII;

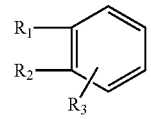 II

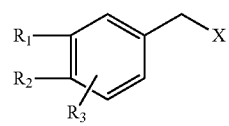 VII wherein X is a halogen atom selected from Cl, Br and I;

b) contacting the resulting reaction mass containing compound of Formula VII with hexamethylenetetramine to obtain a complex of Formula VIII

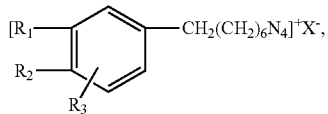 VIII wherein a molar ratio of said hexamethylenetetramine to said compound of Formula VII is greater than 1;

c) decomposing the complex of Formula VIII to produce the compound of Formula 1, comprising contacting a reaction mass of step b) with acid, or base or salt or mixtures thereof in biphasic reaction, wherein said acid or base or salt or mixture thereof is selected from the group consisting of i) aqueous acetic acid, ii) a mixture of aqueous acetic acid and mineral acids wherein said mineral acid comprises one of phosphoric acid, sulfuric acid, hydrochloric acid, nitric acid and mixtures thereof, iii) a mixture of organic acids selected from the group consisting of acetic acid, chloroacetic acid, a mixture of aqueous acetic acid and iv) alkali metal salts selected from the group consisting of sodium acetate, sodium phosphates, and mixtures thereof, and v) a combination thereof, wherein an initial acid concentration is in a range of about 20% to about 70%, d) separating an organic solvent layer of a biphasic reaction mass of step c) containing compound of Formula 1;

e) isolating substantially pure compound of Formula 1 in yield of about 80% comprising recovering the organic solvent from said organic solvent layer of step d) followed by purification of a crude mass by standard purification process, wherein said process is carried out without solvent recovery, isolation and/or purification at any intermediate stage.

2. The process as in claim 1, wherein the organic solvent is an aromatic hydrocarbon comprising at least one of benzene, toluene, and xylene.

3. The process as in claim 2, wherein the organic solvent is toluene.

4. The process as in claim 1, wherein the acid or base or salt or mixture thereof consists of said mixture of aqueous acetic acid and mineral acids and the mineral acid is HCl.

5. The process as in claim 1, wherein the starting material is compound of Formula III and the corresponding alkoxy substituted benzaldehyde is represented by compound of Formula IV

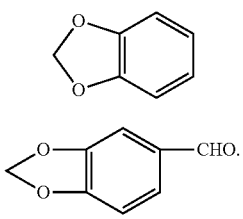

III

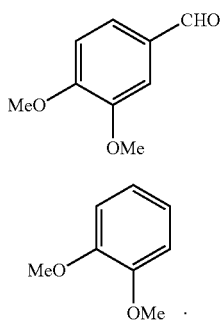

IV

6. The process as in claim 1, wherein the starting material is compound of Formula XII and the corresponding alkoxy substituted benzaldehyde is represented by compound of Formula V

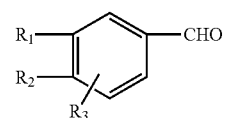

[V]

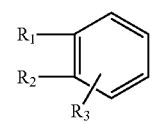

[XII]

7. The process as in claim 1, wherein the starting material is compound of Formula XV and the corresponding alkoxy substituted benzaldehyde is represented by compound of Formula VI

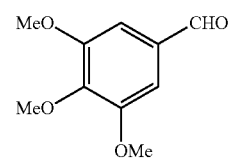

[VI]

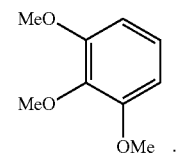

[XV]

8. The process as in claim 1, wherein reaction temperature in said steps b) and c) is 80° C.±10%.

9. A process for the preparation of alkoxy substituted benzaldehydes of Formula 1 from corresponding alkoxy benzenes of Formula II, $R_1$—⬡—CHO
$R_2$—
$R_3$

I $R_1$—⬡
$R_2$—
$R_3$

II wherein $R_1$, $R_2$ and $R_3$ are independent of each other, $R_2$ represents alkoxy group —OR, wherein R is a substituted or unsubstituted C1-C4 alkyl group, substituted or unsubstituted C3-C6 cycloalkyl group, or $R_1$ and $R_2$ together jointly form an alkylenedioxy group represented by —O—(CH2)n-O— wherein n is 1, 2, 3 or 4, $R_1$ represents H, R or —OR, wherein R is a substituted or unsubstituted C1-C4 alkyl group, substituted or unsubstituted C3-C6 cycloalkyl group, or $R_1$ and $R_2$ together jointly form an alkylenedioxy group represented by —O—(CH2)n-O— wherein n is 1, 2, 3 or 4, and $R_3$ is a substituent at any position of aromatic ring other than position 1, 3 and 4 and represents H, R, —OR, wherein R is a substituted or unsubstituted C1-C4 alkyl group, or substituted or unsubstituted C3-C6 cycloalkyl group, or $R_3$ represents halogen selected from Cl, Br, I, or nitrogen containing group selected from CrN, NO2, NH2, —CONH2, in a straight-through chemical process, said process comprising the steps of:

a) halomethylation of starting material represented by compound of Formula II in an organic solvent to obtain the compound of Formula VII;

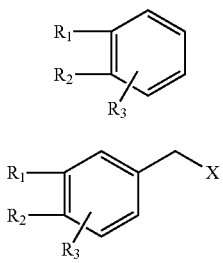

II

VII wherein X is a halogen atom selected from Cl, Br and I;

b) contacting the resulting reaction mass containing compound of Formula VII with hexamethylenetetramine to obtain a complex of Formula VIII

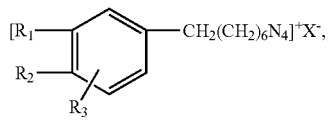

VIII wherein a molar ratio of said hexamethylenetetramine to said compound of Formula VII is greater than 1;

c) decomposing said complex of Formula VIII to produce the compound of Formula 1, comprising contacting said reaction mass of step b) with aqueous acetic acid; or a mixture of aqueous acetic acid and mineral acids wherein the mineral acid is selected from the group consisting of phosphoric acid, sulfuric acid, hydrochloric acid, nitric acid and mixtures thereof; or a mixture of aqueous acetic acid and alkali metals selected from the group consisting of sodium acetate, sodium phosphates and mixtures thereof; or, a combination thereof; wherein initial acid concentration is in the range of about 20% to 70%, and maintaining pH in a range of about 2 to about 6, d) separating an organic solvent layer of a biphasic reaction mass of step c) containing compound of Formula 1;

e) isolating substantially pure compound of Formula 1 in yield of about 80% comprising recovering the organic solvent from the said organic solvent layer of step d) followed by purification of a crude mass by standard purification process.

10. The process as in claim 9, wherein the organic solvent is an aromatic hydrocarbon comprising at least one of benzene, toluene, and xylene.

11. The process as in claim 9, wherein reaction temperature in said steps b) and c) is 80° C.±10%.

* * * * *